United States Patent
Xu

(10) Patent No.: US 11,353,466 B2
(45) Date of Patent: Jun. 7, 2022

(54) METHODS AND COMPOSITIONS FOR QUANTIFYING HEMOGLOBIN

(71) Applicant: CELLICS THERAPEUTICS, INC., San Diego, CA (US)

(72) Inventor: Weidong Xu, San Diego, CA (US)

(73) Assignee: CELLICS THERAPEUTICS, INC., San Diego, CA (US)

(*) Notice: Subject to any disclaimer, the term of this patent is extended or adjusted under 35 U.S.C. 154(b) by 128 days.

(21) Appl. No.: 16/962,186

(22) PCT Filed: Jan. 15, 2019

(86) PCT No.: PCT/US2019/013712
§ 371 (c)(1),
(2) Date: Jul. 14, 2020

(87) PCT Pub. No.: WO2019/143637
PCT Pub. Date: Jul. 25, 2019

(65) Prior Publication Data
US 2021/0011033 A1     Jan. 14, 2021

Related U.S. Application Data

(60) Provisional application No. 62/619,043, filed on Jan. 18, 2018.

(51) Int. Cl.
*G01N 33/72* (2006.01)
*C12Q 1/28* (2006.01)
*G01N 33/52* (2006.01)

(52) U.S. Cl.
CPC ............ *G01N 33/725* (2013.01); *C12Q 1/28* (2013.01); *G01N 33/52* (2013.01)

(58) Field of Classification Search
CPC ................ G01N 33/725; G01N 33/52; G01N 33/54346; G01N 33/721; C12Q 1/28
See application file for complete search history.

(56) References Cited

U.S. PATENT DOCUMENTS

| | | | |
|---|---|---|---|
| 7,235,378 B2 | 6/2007 | Yonehara | |
| 7,381,797 B2 | 6/2008 | Woerner et al. | |
| 2003/0073150 A1* | 4/2003 | Woerner | C12Q 1/28 |
| | | | 435/7.92 |
| 2013/0337066 A1 | 12/2013 | Zhang et al. | |
| 2017/0274059 A1* | 9/2017 | Zhang | A61K 9/0014 |

FOREIGN PATENT DOCUMENTS

WO      2016/028965 A1    2/2016

OTHER PUBLICATIONS

International Search Report for international patent application PCT/US19/13712 (WO2019143637), dated Jul. 25, 2019, 3 pages.
Written Opinion of the International Searching Authority for international patent application PCT/US19/13712 (WO2019143637), dated Jul. 25, 2019, 4 pages.

(Continued)

*Primary Examiner* — Jennifer Wecker
*Assistant Examiner* — Michael Paul Shimek
(74) *Attorney, Agent, or Firm* — Rimon, P.C.

(57) ABSTRACT

The present invention relates to methods and compositions for quantifying hemoglobin using, inter alia, a peroxidase substrate and hydrogen peroxide.

22 Claims, 4 Drawing Sheets

4-Parameter Curve Fit of Fluorogenic Hemoglobin Assay Standard Curve with Hemoglobin as Standards in Target Range of 5 – 100 µg/ml

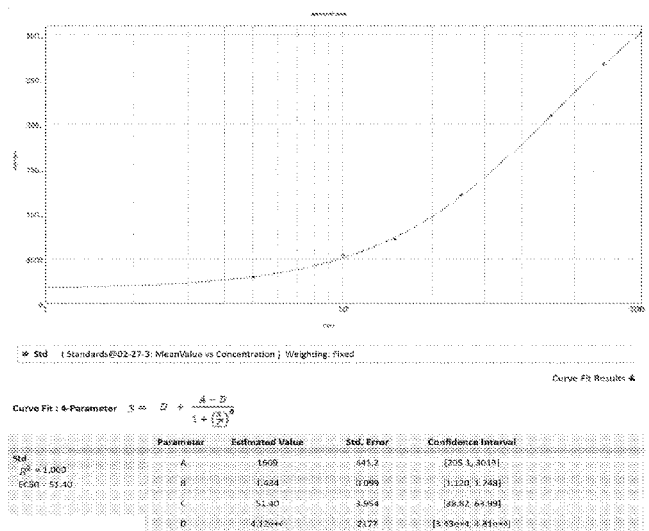

(56) References Cited

OTHER PUBLICATIONS

International Preliminary Report on Patentability for international patent application PCT/US19/13712 (WO2019143637), dated Jul. 21, 2020, 5 pages.
Huy et al., "An improved colorimetric method for quantitation of heme using tetramethylbenzidine as substrate," Anal. Biochem, 344:289-291 (2005) doi:10.1016/j.ab.2005.06.022.

\* cited by examiner

Figure 1    Specificity of fluorogenic Hemoglobin Assay

| Specificity | Reading 1 (FU) | Reading 2 (FU) | Reading 3 (FU) | Average | Acceptance criteria (% interference) | % interference | Pass/Fail |
|---|---|---|---|---|---|---|---|
| Value of lowest standards (2.5 ug/ml) | 2293.4 | 2179.4 | 2261.3 | 2244.70 | | | |
| Interference of Standard dilution solution | 432.54 | 421.75 | 369.91 | 408.07 | <25% | 18.18 | Pass |
| Interference of Matrix control P1 | 325.94 | 318.21 | 304.86 | 316.34 | <25% | 14.09 | Pass |
| Interference of Matrix control P2 | 265.7 | 261.94 | 263.07 | 263.57 | <25% | 11.74 | Pass |

Figure 2    4-Parameter Curve Fit of Fluorogenic Hemoglobin Assay Standard Curve with Hemoglobin as Standards in Target Range of 5 – 100 μg/ml

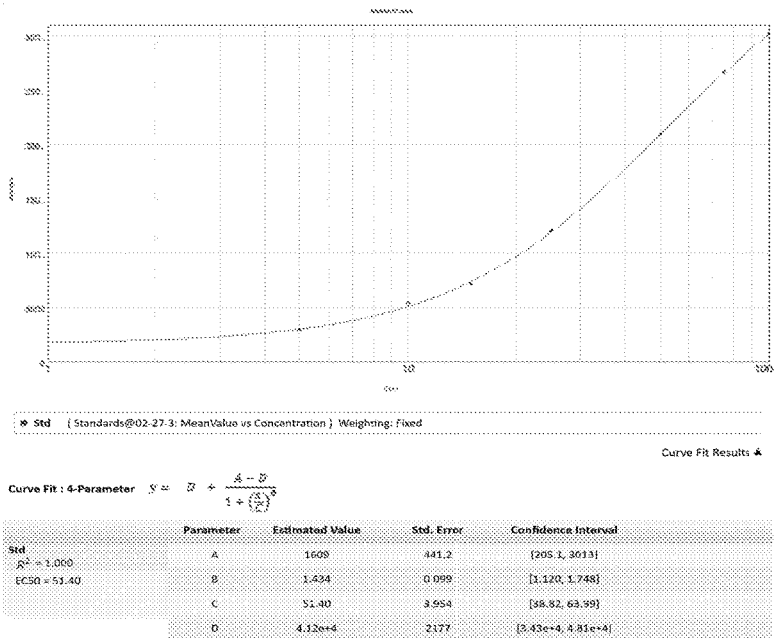

Figure 3: Fluorogenic Hemoglobin Assay Results from Triplicates on Standard Solutions Shown NMT 5% Relative Standard Deviations (CV) and Calculated Accuracy within 90 – 110%

Standards

| Sample | Concentration µg/mL | BackCalcConc | Value | MeanValue | SD | CV | Accuracy (%) |
|---|---|---|---|---|---|---|---|
| Std-01 | 5.000 | 5.142 | 3014.110 | 2873.295 | 183.720 | 6.4 | 95.178 |
| | | 4.946 | 2940.297 | | | | |
| | | 4.188 | 2665.478 | | | | |
| Std-02 | 10.000 | 10.981 | 5507.661 | 5339.171 | 199.603 | 3.7 | 106.116 |
| | | 10.726 | 5391.122 | | | | |
| | | 10.128 | 5118.729 | | | | |
| Std-03 | 15.000 | 14.790 | 7287.465 | 7119.542 | 179.834 | 2.5 | 96.227 |
| | | 14.480 | 7141.372 | | | | |
| | | 14.031 | 6929.789 | | | | |
| Std-04 | 25.000 | 25.570 | 12241.728 | 12085.040 | 162.897 | 1.3 | 100.847 |
| | | 25.238 | 12096.818 | | | | |
| | | 24.828 | 11916.574 | | | | |
| Std-05 | 50.000 | 50.146 | 21048.947 | 20964.950 | 107.473 | 0.5 | 99.702 |
| | | 49.980 | 21002.064 | | | | |
| | | 49.426 | 20843.839 | | | | |
| Std-06 | 75.000 | 76.161 | 26837.593 | 26683.970 | 211.550 | 0.8 | 100.380 |
| | | 75.779 | 26771.636 | | | | |
| | | 73.916 | 26442.679 | | | | |
| Std-07 | 100.000 | 102.458 | 30463.607 | 30166.250 | 258.032 | 0.9 | 99.829 |
| | | 98.375 | 30001.310 | | | | |
| | | 98.653 | 30033.833 | | | | |

Figure 4: Results of Nine Replicates of Different Diluted Packed RBCs, TFF RBC Membrane and Nanosponge Assayed Demonstrated Less Than 5% Relative Standard Deviations.

| Sample | Value | Result | MeanResult | SD | CV | Dilution | AdjResult |
|---|---|---|---|---|---|---|---|
| B01 | 18784.695 | 33.981 | 32.770 | 0.631 | 1.4 | 8800.0 | 288378.188 |
| | 18410.723 | 33.029 | | | | | |
| | 18446.049 | 33.118 | | | | | |
| | 18164.023 | 32.410 | | | | | |
| | 18026.965 | 32.069 | | | | | |
| | 18126.344 | 32.316 | | | | | |
| | 18530.740 | 33.332 | | | | | |
| | 18095.334 | 32.239 | | | | | |
| | 18175.377 | 32.438 | | | | | |
| NS63-4 | 9150.026 | 13.623 | 13.412 | 0.257 | 1.6 | 4.0 | 53.647 |
| | 8955.651 | 13.277 | | | | | |
| | 8879.407 | 13.141 | | | | | |
| | 9125.620 | 13.579 | | | | | |
| | 8977.302 | 13.315 | | | | | |
| | 8855.636 | 13.099 | | | | | |
| | 9307.279 | 13.904 | | | | | |
| | 9059.094 | 13.461 | | | | | |
| | 8972.753 | 13.307 | | | | | |

Figure 5: Calculated Accuracy of Series Dilutions of Lowest Standards hemoglobin at 10 µg/ml Shows the LOD Around 2.5 µg/ml

| Sample | Concentration µg/ml | BackCalcConc | Value | MeanValue | SD | CV | Accuracy (%) |
|---|---|---|---|---|---|---|---|
| Std-1.25 | 1.250 | 1.092 | 2665.214 | 2493.219 | 130.018 | 5.2 | 57.449 |
| | | 0.596 | 2435.548 | | | | |
| | | 0.536 | 2409.302 | | | | |
| | | 1.044 | 2641.946 | | | | |
| | | 0.652 | 2460.261 | | | | |
| | | 0.388 | 2347.042 | | | | |
| Std-10 | 10.000 | 10.645 | 8043.312 | 7713.643 | 166.111 | 2.2 | 100.643 |
| | | 9.868 | 7601.999 | | | | |
| | | 10.059 | 7710.562 | | | | |
| | | 9.913 | 7627.798 | | | | |
| | | 9.992 | 7672.615 | | | | |
| | | 9.909 | 7625.573 | | | | |
| Std-2.5 | 2.500 | 2.458 | 3369.567 | 3116.953 | 261.173 | 8.4 | 79.009 |
| | | 2.092 | 3174.078 | | | | |
| | | 2.167 | 3213.878 | | | | |
| | | 2.107 | 3181.825 | | | | |
| | | 2.055 | 3154.320 | | | | |
| | | 0.973 | 2608.052 | | | | |
| Std-5 | 5.000 | 5.423 | 5040.401 | 4860.823 | 98.947 | 2.0 | 102.191 |
| | | 4.961 | 4774.414 | | | | |
| | | 5.153 | 4884.872 | | | | |
| | | 5.084 | 4845.192 | | | | |
| | | 5.083 | 4844.772 | | | | |
| | | 4.954 | 4770.484 | | | | |

Figure 6: Results of Fluorogenic Hemoglobin Assay with 1:2 Series Diluted of TFF RBC Membrane and Nanosponge in Six Replicates Demonstrate the LOQ at 14 µg/ml

| Sample | Value | Result | MeanResult | SD | CV | Dilution | AdjResult |
|---|---|---|---|---|---|---|---|
| MA49-1 | 14879.675 | 30.002 | 29.171 | 0.536 | 1.8 | 2.0 | 58.343 |
| | 14654.606 | 29.411 | | | | | |
| | 14586.755 | 29.234 | | | | | |
| | 14558.080 | 29.159 | | | | | |
| | 14412.970 | 28.781 | | | | | |
| | 14282.860 | 28.443 | | | | | |
| MA49-2 | 9783.736 | 17.232 | 16.807 | 0.373 | 2.2 | 4.0 | 67.230 |
| | 9778.575 | 17.219 | | | | | |
| | 9654.817 | 16.914 | | | | | |
| | 9457.951 | 16.428 | | | | | |
| | 9550.647 | 16.657 | | | | | |
| | 9444.842 | 16.395 | | | | | |
| MA49-3 | 6540.654 | 8.831 | 8.407 | 0.242 | 2.9 | 8.0 | 67.254 |
| | 6405.119 | 8.440 | | | | | |
| | 6336.624 | 8.240 | | | | | |
| | 6409.983 | 8.454 | | | | | |
| | 6374.343 | 8.351 | | | | | |
| | 6297.130 | 8.124 | | | | | |
| MA49-4 | 4680.166 | 2.333 | 1.375 | 0.763 | 55.5 | 16.0 | 21.997 |
| | 4360.581 | Range? | | | | | |
| | 4349.076 | Range? | | | | | |
| | 4553.590 | 1.628 | | | | | |
| | 4448.529 | 0.891 | | | | | |
| | 4421.345 | 0.647 | | | | | |

| Sample | Value | Result | MeanResult | SD | CV | Dilution | AdjResult |
|---|---|---|---|---|---|---|---|
| NS63-4 | 6602.080 | 13.999 | 13.602 | 0.388 | 2.9 | 4.0 | 54.406 |
| | 6492.268 | 13.728 | | | | | |
| | 6563.459 | 13.904 | | | | | |
| | 6398.308 | 13.495 | | | | | |
| | 6428.848 | 13.571 | | | | | |
| | 6163.414 | 12.913 | | | | | |
| NS63-5 | 3952.062 | 7.197 | 6.646 | 0.440 | 6.6 | 8.0 | 53.167 |
| | 3849.942 | 6.914 | | | | | |
| | 3813.604 | 6.812 | | | | | |
| | 3728.195 | 6.572 | | | | | |
| | 3688.667 | 6.460 | | | | | |
| | 3501.589 | 5.922 | | | | | |
| NS63-6 | 2545.366 | 2.852 | 2.324 | 0.364 | 15.7 | 16.0 | 37.180 |
| | 2349.270 | 2.089 | | | | | |
| | 2303.105 | 1.894 | | | | | |
| | 2415.221 | 2.355 | | | | | |
| | 2434.019 | 2.429 | | | | | |
| | 1324.574 | Range? | | | | | |
| NS63-7 | 1794.301 | Range? | Range? | Range? | Range? | 32.0 | Range? |
| | 1590.999 | Range? | | | | | |
| | 1637.111 | Range? | | | | | |
| | 1802.312 | Range? | | | | | |
| | 1660.451 | Range? | | | | | |
| | 1574.714 | Range? | | | | | |

Figure 7: 1:4 Diluted Nanosponge NS63 Assayed in Three Different Dates Shows the Reliability of the Assay

| Sample | Value | Result | MeanResult | SD | CV | Dilution | AdjResult |
|---|---|---|---|---|---|---|---|
| NS63-4 | 6602.080 | 13.999 | 13.602 | 0.388 | 2.9 | 4.0 | 54.406 |
| | 6492.268 | 13.728 | | | | | |
| | 6563.459 | 13.904 | | | | | |
| | 6398.308 | 13.495 | | | | | |
| | 6428.848 | 13.571 | | | | | |
| | 6163.414 | 12.913 | | | | | |

| Sample | Value | Result | MeanResult | SD | CV | Dilution | AdjResult |
|---|---|---|---|---|---|---|---|
| NS63-4 | 10761.914 | 14.795 | 13.841 | 0.549 | 4.0 | 4.0 | 55.364 |
| | 10413.809 | 13.744 | | | | | |
| | 10602.971 | 14.318 | | | | | |
| | 10378.453 | 13.636 | | | | | |
| | 10144.963 | 12.916 | | | | | |
| | 10459.731 | 13.884 | | | | | |
| | 10362.957 | 13.589 | | | | | |
| | 10447.258 | 13.846 | | | | | |

| Sample | Value | Result | MeanResult | SD | CV | Dilution | AdjResult |
|---|---|---|---|---|---|---|---|
| NS63-4 | 9150.026 | 13.623 | 13.412 | 0.257 | 1.9 | 4.0 | 53.647 |
| | 8955.651 | 13.277 | | | | | |
| | 8879.407 | 13.141 | | | | | |
| | 9125.620 | 13.579 | | | | | |
| | 8977.302 | 13.315 | | | | | |
| | 8855.636 | 13.099 | | | | | |
| | 9307.279 | 13.904 | | | | | |
| | 9059.094 | 13.461 | | | | | |
| | 8972.753 | 13.307 | | | | | |

METHODS AND COMPOSITIONS FOR QUANTIFYING HEMOGLOBIN

I. CROSS-REFERENCE TO RELATED APPLICATION

The present application is a U.S. national phase filing of International Patent Application Serial No. PCT/US2019/013712, filed on Jan. 15, 2019, entitled "Methods and Compositions for Quantifying Hemoglobin," which claims priority to U.S. provisional patent application No. 62/619,043, filed on Jan. 18, 2018 The contents and disclosures of the above applications are incorporated herein by reference in their entireties for all purposes.

II. FIELD OF THE INVENTION

The present invention relates to methods and compositions for quantifying hemoglobin using, inter alia, a peroxidase substrate and hydrogen peroxide.

III. BACKGROUND OF THE INVENTION

Hemoglobin (Hb) is an iron-containing metalloprotein that serves as the primary means of oxygen transport in vertebrates. Hemoglobin is primarily found in red blood cells where it makes up to 97% of the cell's dry content. Hemoglobin can also be found in other tissues where it serves as an antioxidant. Hemin is the essential part of hemoglobin molecule. Huy et al., *Anal. Biochem.*, 344:289-291 (2005) describes a colorimetric method for quantitation of heme using tetramethylbenzidine as substrate.

New and improved methods and compositions for quantifying hemoglobin, especially at low level, are needed. The present invention addresses these and other related needs in the art.

IV. SUMMARY OF THE INVENTION

In one aspect, the present invention provides a method for quantifying hemoglobin in a sample, which method comprises: a) contacting a sample containing or suspected of containing hemoglobin with a peroxidase substrate and hydrogen peroxide, under suitable conditions, for allowing oxidation of said peroxidase substrate to form an oxidation product; and b) assessing said peroxidase substrate and/or said oxidation product to quantify hemoglobin in said sample.

In another aspect, the present invention provides a kit for quantifying hemoglobin in a sample, which kit comprises: a) a peroxidase substrate; b) hydrogen peroxide; and c) a solution or suspension that has basic pH and/or contains a surfactant for preparing a sample containing or suspected of containing hemoglobin.

In still another aspect, the present invention provides a system for quantifying hemoglobin in a sample, which system comprises: a) a kit described above; and b) means for assessing a peroxidase substrate and/or an oxidation product of said peroxidase substrate, e.g., 7-hydroxyphenoxazin-3-one, to quantify hemoglobin in said sample.

V. BRIEF DESCRIPTION OF THE DRAWINGS

FIG. 1 illustrates specificity of an exemplary hemoglobin assay.

FIG. 2 illustrates 4-parameter Curve fit of an exemplary fluorogenic hemoglobin assay standard curve with hemoglobin as standards in target range of 5-100 µg/ml.

FIG. 3 illustrates exemplary fluorogenic hemoglobin assay results from triplicates on standard solutions shown NMT (no more than) 5% relative standard deviations (CV) and calculated accuracy within 90-110%.

FIG. 4 illustrates exemplary results of nine replicates of different diluted packed RBCs, TFF RBC membrane and nanosponge showing less than 5% relative standard deviations.

FIG. 5 illustrates exemplary calculated accuracy of serial dilutions of low standards hemoglobin at 10 µg/ml showing a limit of detection (LOD) around 2.5 µg/ml.

FIG. 6 illustrates results of exemplary fluorogenic hemoglobin assay with 1:2 serial diluted TFF RBC membrane and nanosponge in six replicates showing a LOQ at 14 µg/ml.

FIG. 7 illustrates 1:4 diluted nanosponge NS63 assayed in three different dates showing reliability of the hemoglobin assay.

VI. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Laboratory Manual*, $2^{nd}$ ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and *Remington, The Science and Practice of Pharmacy*, $20^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including"

and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: The term "nanoparticle" as used herein refers to nanostructure, particles, vesicles, or fragments thereof having at least one dimension (e.g., height, length, width, or diameter) of between about 1 nm and about 10 μm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Methods for Quantifying Hemoglobin

In one aspect, the present invention provides a method for quantifying hemoglobin in a sample, which method comprises: a) contacting a sample containing or suspected of containing hemoglobin with a peroxidase substrate and hydrogen peroxide, under suitable conditions, for allowing oxidation of said peroxidase substrate to form an oxidation product; and b) assessing said peroxidase substrate and/or said oxidation product to quantify hemoglobin in said sample.

Any suitable peroxidase substrate can be used in the present methods. In some embodiments, the peroxidase substrate is a chromogenic/colorimetric substrate, a fluorogenic substrate or a chemiluminescence substrate. In other embodiments, the peroxidase substrate is 10-acetyl-3,7-dihydroxyphenoxazine (ADHP), 3,3',5,5'-Tetramethylbenzidine (TMB), 3,3'-Diaminobenzidine (DAB), 2,2'-azino-bis (3-ethylbenzothiazoline-6-sulphonic acid) (ABTS), o-phenylenediamine, e.g., o-phenylenediamine dihydrochloride (OPD), 3-amino-9-ethylcarbazole (AEC), homovanillic acid or luminol, etc.

The present methods can be used to quantify hemoglobin in any suitable sample. In some embodiments, the sample is derived from a vertebrate. The vertebrate can be a mammal, e.g., a non-human mammal or a human. In other embodiments, the sample is derived from vertebrate blood. For example, the sample can be derived from mammalian blood. In another example, the sample can be derived from non-human mammalian blood. In still another example, the sample can be derived from human blood. In still other embodiments, the sample comprises a cellular membrane preparation from a hemoglobin-containing cell. For example, the hemoglobin-containing cell can be a red blood cell. The red blood cell can be a mammalian red blood cell, e.g., a non-human mammalian red blood cell or a human red blood cell.

The present methods can be used to quantify hemoglobin in a sample that contains a cellular membrane preparation from any suitable human red blood cell. The human red blood cell can comprise any suitable blood type antigen. In some embodiments, the human red blood cell can comprise a blood type antigen in a major blood group system or a combination thereof. For example, the major blood group system can be the ABO blood group system and the blood type antigen can be the antigen that determines the A blood type, B blood type or AB blood type. In another example, the major blood group system can be the Rh blood group system. In still another example, the blood type antigen that is missing or potentially missing on red blood cells of the recipient can be antigen D, C, c, E, or e. In other embodiments, the cellular membrane of the nanoparticle can comprise a blood type antigen in a minor or rare blood group system that is missing or potentially missing on red blood cells of the recipient.

In other embodiments, the human red blood cell can comprise a blood type antigen in a blood group system including ABO, MNS, P1PK, Rh, Lutheran, Kell, Lewis, Duffy, Kidd, Diego, Yt, Xg, Scianna, Dombrock, Colton, Landsteiner-Wiener, Chido/Rodgers, H, Kx, Gerbich, Knops, Indian, Ok, Raph, John Milton Hagen, I, Globoside, Gill, Rh-associated glycoprotein, FORS, JR, LAN, Vel, ER, Ata Antigen, AnWj antigen, Sda Antigen, Batty (By), Biles (Bi), Box (Bx$^a$), Christiansen (Chr$^a$), HJK, HOFM, JFV, JONES, Jensen (Je$^a$), Katagiri (Kg), Livesay (Li$^a$), Milne, Oldeide (Ol$^a$), Peters (Pt$^a$), Rasmussen (RASM), Reid (Re$^a$), REIT, SARA, Torkildsen (To$^a$) or Bg (Bennett-Goodspeed) blood group system. In still other embodiments, the human red blood cell can comprise a blood type antigen in a blood group system listed in the following Table 1.

TABLE 1

Exemplary blood group systems

| No. | System name | System symbol | Gene name(s)* | Chromosomal location | CD numbers |
|---|---|---|---|---|---|
| 001 | ABO | ABO | ABO | 9q34.2 | |
| 002 | MNS | MNS | GYPA, GYPB, GYPE | 4q31.21 | CD235 |
| 003 | P1PK | P1PK | A4GALT | 22q13.2 | |
| 004 | Rh | RH | RHD, RHCE | 1p36.11 | CD240 |
| 005 | Lutheran | LU | LU | 19q13.32 | CD239 |
| 006 | Kell | KEL | KEL | 7q34 | CD238 |
| 007 | Lewis | LE | FUT3 | 19p13.3 | |
| 008 | Duffy | FY | DARC | 1q23.2 | CD234 |
| 009 | Kidd | JK | SLC14A1 | 18q12.3 | |
| 010 | Diego | DI | SLC4A1 | 17q21.31 | CD233 |
| 011 | Yt | YT | ACHE | 7q22.1 | |
| 012 | Xg | XG | XG, MIC2 | Xp22.33 | CD99† |
| 013 | Scianna | SC | ERMAP | 1p34.2 | |
| 014 | Dombrock | DO | ART4 | 12p12.3 | CD297 |
| 015 | Colton | CO | AQP1 | 7p14.3 | |
| 016 | Landsteiner-Wiener | LW | ICAM4 | 19p13.2 | CD242 |
| 017 | Chido/Rodgers | CH/RG | C4A, C4B | 6p21.3 | |
| 018 | H | H | FUT1 | 19q13.33 | CD173 |
| 019 | Kx | XK | XK | Xp21.1 | |
| 020 | Gerbich | GE | GYPC | 2q14.3 | CD236 |
| 021 | Cromer | CROM | CD55 | 1q32.2 | CD55 |
| 022 | Knops | KN | CR1 | 1q32.2 | CD35 |
| 023 | Indian | IN | CD44 | 11p13 | CD44 |
| 024 | Ok | OK | BSG | 19p13.3 | CD147 |
| 025 | Raph | RAPH | CD151 | 11p15.5 | CD151 |
| 026 | John Milton Hagen | JMH | SEMA7A | 15q24.1 | CD108 |
| 027 | I | I | GCNT2 | 6p24.2 | |
| 028 | Globoside | GLOB | B3GALT3 | 3q26.1 | |
| 029 | Gill | GIL | AQP3 | 9p13.3 | |
| 030 | Rh-associated glycoprotein | RHAG | RHAG | 6p21-qter | CD241 |

TABLE 1-continued

Exemplary blood group systems

| No. | System name | System symbol | Gene name(s)* | Chromosomal location | CD numbers |
|---|---|---|---|---|---|
| 031 | FORS | FORS | GBGT1 | 9q34.13 | |
| 032 | JR | JR | ABCG2 | 4q22 | |
| 033 | LAN | LAN | ABCB6 | 2q36 | |

*As recognized by the HUGO Gene Nomenclature Committee http://www.genenames.org/.

In some embodiments, the present methods can be used to quantify hemoglobin in a sample that contains a cellular membrane preparation from a hemoglobin-containing cell that is a non-erythroid cell. For example, the non-erythroid cell can be an A9 dopaminergic neuron, a macrophage, an alveolar cell, or a mesangial cell.

The present methods can be used to quantify hemoglobin in a sample that contains a cellular membrane coated nanoparticle, said nanoparticle comprising an inner core comprising a non-cellular material and an outer surface comprising a cellular membrane derived from a hemoglobin-containing cell. The present methods can be used to quantify hemoglobin in a sample that contains any suitable nanoparticle. In some embodiments, the inner core of the nanoparticle can comprise a biocompatible and/or a synthetic material, such as poly(lactic-c-glycolic acid) (PLGA), polylactic acid (PLA), polyglycolic acid (PGA), polycaprolactone (PCL), polylysine, polyglutamic acid, or a hydrophobic polymer that coils when switched from an organic solvent to an aqueous phase, e.g., water. In other embodiments, the inner core of the nanoparticle supports the outer surface.

The nanoparticle can comprise any suitable cellular membrane derived from a hemoglobin-containing cell, e.g., a red blood cell. For example, the nanoparticle can comprise a plasma membrane or an intracellular membrane derived from a hemoglobin-containing cell, e.g., a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a red blood cell. In some embodiments, the cellular membrane comprises a naturally occurring plasma membrane derived from a red blood cell, e.g., a naturally occurring plasma membrane derived from a human red blood cell. In some embodiments, the cellular membrane can be derived from a non-erythroid cell, e.g., an A9 dopaminergic neuron, a macrophage, an alveolar cell, or a mesangial cell.

The nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the recipient or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, an imaging agent, or a combination thereof. In another example, the releasable cargo can be a metallic particle, a polymeric particle, a dendrimer particle, or an inorganic particle.

The nanoparticle can have any suitable size. For example, the nanoparticle can have a diameter from about 10 nm to about 10 µm, preferably about 50 nm to about 150 nm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of a hemoglobin-containing cell, e.g., a red blood cell, from which the cellular membrane is derived. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the hemoglobin-containing cell, e.g., the red blood cell, from which the cellular membrane is derived. In some embodiments, the nanoparticle comprises a plasma membrane derived from a hemoglobin-containing cell, e.g., a red blood cell, and the nanoparticle substantially lacks hemoglobin. For example, the nanoparticle can lack at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular membrane or the constituents of the cellular membrane including primary, secondary, tertiary and/or quaternary structure of the cellular membrane, or the constituents of the cellular membrane. In some embodiments, the nanoparticle substantially maintains activity of the cellular membrane or the constituents of the cellular membrane including binding activity, receptor activity and/or enzymatic activity of the cellular membrane, or the constituents of the cellular membrane.

In some embodiments, the nanoparticle is biocompatible or biodegradable. For example, the inner core of the nanoparticle comprises PLGA and the outer surface of the nanoparticle comprises a plasma membrane derived from a cell, e.g., a red blood cell.

The nanoparticle can have any suitable half-life in vivo. For example, the nanoparticle can has a half-life in blood circulation in vivo for at least about 2-5 times of the half-life of a PEG-coated, comparable nanoparticle, or has a half-life in blood circulation in vivo for at least about 1 to about 40 hours.

In some embodiments, the nanoparticle substantially lacks immunogenicity to a subject, a mammal, a non-human mammal or a human, to which the nanoparticle is configured to administer. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to be treated.

The outer surface of the nanoparticle can comprise a hybrid membrane comprising a cellular membrane derived from a cell and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane and about 95-99% (w/w) of a synthetic membrane, about 11-25% (w/w) of a cellular membrane and about 75-89% (w/w) of a synthetic membrane, about 50% (w/w) of a cellular membrane and about 50% (w/w) of a synthetic membrane, about 51-75% (w/w) of a cellular membrane and about 49-25% (w/w) of a synthetic membrane, or about 90-99% (w/w) of a cellular membrane and about 1-10% (w/w) of a synthetic membrane.

The present methods can be used to quantify any suitable hemoglobin in a sample. For example, the present methods can be used to quantify any suitable type or subtype hemoglobin, or a combination thereof, in a sample. In another example, the present methods can be used to quantify a total level of hemoglobin in a sample.

The present methods can be used to quantify any suitable vertebrate or mammalian hemoglobin, e.g., a non-human hemoglobin. For example, the present methods can be used to quantify human hemoglobin in a sample. In some embodiments, the human hemoglobin is a human embryonic hemoglobin, a human fetal hemoglobin, or a human hemoglobin after birth. The human embryonic hemoglobin can be Gower 1 ($\zeta_2\varepsilon_2$), Gower 2 ($\alpha_2\varepsilon_2$), hemoglobin Portland I ($\zeta_2\gamma_2$), hemoglobin Portland II ($\zeta_2\beta_2$) or a combination thereof. The human fetal hemoglobin can be hemoglobin F ($\alpha_2\gamma_2$). The human hemoglobin after birth can be hemoglobin A ($\alpha_2\beta_2$), hemoglobin A2 ($\alpha_2\delta_2$), hemoglobin F ($\alpha_2\gamma_2$) or a combination thereof. The present methods can be used to quantify any suitable type or subtype human hemoglobin, or a combination thereof, in a sample. The present methods can also be used to quantify a total level of human hemoglobin in a sample.

Before contacted with a peroxidase substrate and hydrogen peroxide, a sample can be subjected to any suitable treatment. For example, a sample can be incubated in a solution or suspension that has basic pH and/or contains a detergent before being contacted with a peroxidase substrate, e.g., ADHP, and hydrogen peroxide.

The solution or suspension can have any suitable basic pH. For example, the solution or suspension can have a pH of 12 or higher, e.g., a pH of 12, 13, or 14. The solution or suspension can have any suitable base, e.g., NaOH, KOH or LiOH. The solution or suspension can have any suitable level or concentration of a base. For example, the solution or suspension can have a base, e.g., NaOH, KOH or LiOH, at a level or concentration from about 0.01 mM to about 500 mM, e.g., at about 0.01 mM, 0.1 mM, 1 mM, 10 mM, 20 mM, 30 mM, 40 mM, 50 mM, 60 mM, 70 mM, 80 mM, 90 mM, 100 mM, 200 mM, 300 mM, 400 mM, or 500 mM, or any subrange thereof.

The solution or suspension can have any suitable detergent or surfactant. For example, the solution or suspension can contain a surfactant, e.g., an anionic surfactant, a cationic surfactant, a zwitterionic surfactant or a nonionic surfactant. The solution or suspension can contain any suitable level or concentration of a detergent or surfactant. For example, the solution or suspension can contain a base, e.g., Triton X-100, at a concentration ranging from about 0.01% (w/w) to about 10% (w/w), e.g., at about 0.01% (w/w), 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), or 10% (w/w), or any subrange thereof.

In some embodiments, the solution or suspension can contain both a base and a detergent or surfactant. For example, the solution or suspension can contain both NaOH and Triton X-100.

The sample can be incubated in the solution or suspension for any suitable time before being contacted with a peroxidase substrate, e.g., ADHP, and hydrogen peroxide. For example, the sample can be incubated in the solution or suspension for at least about 1 minute, e.g., at least about 1 minute, 10 minutes, 20 minutes, 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 24 hours, 2 days, 3 days, 4 days, 5 days, 6 days, 7 days, 8 days, 8 days, 9 days, 10 days, or longer, or any subrange thereof, before being contacted with a peroxidase substrate, e.g., ADHP, and hydrogen peroxide.

The sample can be incubated at any suitable temperature in the solution or suspension for at least 1 minute before being contacted with a peroxidase substrate, e.g., ADHP, and hydrogen peroxide. For example, the sample can be incubated at a temperature ranging from about 0° C. to about 37° C., e.g., at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C. or 37° C., or any subrange thereof, in the solution or suspension for at least 1 minute before being contacted with a peroxidase substrate, e.g., ADHP, and hydrogen peroxide.

In step a), a sample can have any suitable total protein concentration. For example, in step a), the sample has a total protein concentration ranging from 5 μg/m to about 100 mg/ml, e.g., a total protein concentration at about 5 μg/m, 6 μg/m, 7 μg/m, 8 μg/m, 9 μg/m, 10 μg/m, 20 μg/m, 30 μg/m, 40 μg/m, 50 μg/m, 60 μg/m, 70 μg/m, 80 μg/m, 90 μg/m, 100 μg/m, 200 μg/m, 300 μg/m, 400 μg/m, 500 μg/m, 600 μg/m, 700 μg/m, 800 μg/m, 800 μg/m, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, or 100 mg/ml, or any subrange thereof.

In step a), the peroxidase substrate, e.g., ADHP, can have any suitable final concentration. For example, in step a), the peroxidase substrate, e.g., ADHP, can have a final concentration ranging from about 1 μg/ml to about 100 μg/ml, e.g., a final concentration at about 1 μg/m, 2 μg/m, 3 μg/m, 4 μg/m, 5 μg/m, 6 μg/m, 7 μg/m, 8 μg/m, 9 μg/m, 10 μg/m, 20 μg/m, 30 μg/m, 40 μg/m, 50 μg/m, 60 μg/m, 70 μg/m, 80 μg/m, 90 μg/m, 100 μg/m, or any subrange thereof.

In step a), the hydrogen peroxide can have any suitable final concentration. For example, in step a), the hydrogen peroxide can have a final concentration ranging from about 0.001% (w/w) to about 50% (w/w), e.g., a final concentration at about 0.001% (w/w), 0.01% (w/w), 0.1% (w/w), 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), or 50% (w/w), or any subrange thereof.

In step a), the sample can be contacted with the peroxidase substrate, e.g., ADHP, and hydrogen peroxide in a reaction mixture having any suitable pH. For example, in step a), the sample can be contacted with the peroxidase substrate, e.g., ADHP, and hydrogen peroxide in a reaction mixture having a pH ranging from about 5 to about 10, e.g., at pH about 5, 6, 7, 8, 9 or 10, or any subrange thereof. In another example, in step a), the sample is contacted with the peroxidase substrate, e.g., ADHP, and hydrogen peroxide in a reaction mixture having a pH ranging from about 6 to about 8, e.g., at pH about 6, 6.5, 7.0, 7.5, 8.0, or any subrange thereof.

In step a), the sample can be contacted with the peroxidase substrate, e.g., ADHP, and hydrogen peroxide in the reaction mixture at any suitable temperature. For example, in step a), the sample can be contacted with the peroxidase substrate, e.g., ADHP, and hydrogen peroxide in the reaction mixture at a temperature ranging from about 0° C. to about 30° C., e.g., at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C. or any subrange thereof.

The sample can be contacted with the peroxidase substrate, e.g., ADHP, and hydrogen peroxide in the reaction mixture for any suitable time before assessing the peroxidase substrate and/or the oxidation product, e.g., 7-hydroxyphenoxazin-3-one, to quantify hemoglobin in q sample. For example, the sample can be contacted with the peroxidase substrate, e.g., ADHP, and hydrogen peroxide in the reaction mixture for at least about 0.1 minute, e.g., at least about 0.1 minute, 1 minute, 2 minutes, 3 minutes, 4 minutes, 5 minutes, 6 minutes, 7 minutes, 8 minutes, 9 minutes, 10 minutes, 11 minute, 12 minutes, 13 minutes, 14 minutes, 15 minutes, 16 minutes, 17 minutes, 18 minutes, 19 minutes, 20 minutes, 21 minute, 22 minutes, 23 minutes, 24 minutes, 25 minutes, 26 minutes, 27 minutes, 28 minutes, 29 minutes, 30 minutes, 40 minutes, 50 minutes, 1 hour, 2 hours, 3 hours, 4 hours, 5 hours, or longer, or any subrange thereof, before assessing the peroxidase substrate and/or the oxidation product, e.g., 7-hydroxyphenoxazin-3-one, to quantify hemoglobin in a sample.

The peroxidase substrate and/or the oxidation product, e.g., 7-hydroxyphenoxazin-3-one, can be assessed via any suitable detection technique. For example, the peroxidase substrate and/or the oxidation product, e.g., 7-hydroxyphenoxazin-3-one, can be assessed via colorimetric detection and/or fluorescent detection.

The present methods can be used to determine the amount and/or concentration of hemoglobin in a sample. The amount and/or concentration of hemoglobin in a sample can be determined in any suitable manner. For example, the amount and/or concentration of hemoglobin in a sample can be determined by comparing the detection signal assessed in b) with a reference standard generated using heme, hemin or hemoglobin. In some embodiments, the amount and/or concentration of hemoglobin in a sample is determined by comparing the detection signal assessed in b) with a reference standard generated using hemoglobin.

The present methods can have any suitable assay linearity. For example, the present methods can have an assay linearity ranging from about 0.5 µg/ml to about 500 µg/ml of heme, hemin or hemoglobin, e.g., at about 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, or any subrange thereof, of heme, hemin or hemoglobin. In some embodiments, the present methods can have an assay linearity ranging from about 0.5 µg/ml to about 500 µg/ml of hemoglobin, e.g., at about 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, or any subrange thereof, of hemoglobin.

The present methods can have any suitable relative standard deviation (CV). For example, the present methods can have a relative standard deviation (CV) of about 5% or less, e.g., about 5%, 4%, 3%, 2%, 1% or less, or any subrange thereof.

The present methods can have any suitable calculated accuracy. For example, the present methods can have a calculated accuracy ranging from about 90% to about 110%, e.g., about 90%, 91%, 92%, 93%, 94%, 95%, 96%, 97%, 98%, 99%, 100%, 101%, 102%, 103%, 104%, 105%, 106%, 107%, 108%, 109%, 110%, or any subrange thereof.

The present methods can have any suitable limit of detection (LOD). For example, the present methods can have a limit of detection (LOD) of standard hemoglobin at about 5 µg/ml. In another example, the present methods can have a limit of quantitation (LOQ) of hemoglobin at about 10 µg/ml in a sample comprising a cellular membrane preparation from a hemoglobin-containing cell or a sample comprising a cellular membrane coated nanoparticle, said nanoparticle comprising an inner core comprising a non-cellular material and an outer surface comprising a cellular membrane derived from a hemoglobin-containing cell.

The present methods can be used for any suitable purpose. For example, the present methods can be used to monitor hemoglobin amount and/or concentration in a process for reducing or removing hemoglobin. In some embodiments, the process is configured to prepare a cellular membrane preparation from a hemoglobin-containing cell, e.g., a process configured to prepare a red blood cell membrane preparation from the red blood cell. In other embodiments, the process is configured to prepare a cellular membrane coated nanoparticle, said nanoparticle comprising an inner core comprising a non-cellular material and an outer surface comprising a cellular membrane derived from a hemoglobin-containing cell, e.g., a process configured to prepare a red blood cell membrane coated nanoparticle. The cellular membrane coated nanoparticle can be comprised in any suitable composition, e.g., a pharmaceutical composition comprising an effective amount of the cellular membrane coated nanoparticle and a pharmaceutically acceptable carrier and excipient.

C. Kits and Systems for Quantifying Hemoglobin

In another aspect, the present invention provides a kit for quantifying hemoglobin in a sample, which kit comprises: a) a peroxidase substrate; b) hydrogen peroxide; and c) a solution or suspension that has basic pH and/or contains a surfactant for preparing a sample containing or suspected of containing hemoglobin.

Any suitable peroxidase substrate can be used in the present kits. In some embodiments, the peroxidase substrate is a chromogenic/colorimetric substrate, a fluorogenic substrate or a chemiluminescence substrate. In other embodiments, the peroxidase substrate is 10-acetyl-3,7-dihydroxyphenoxazine (ADHP), 3,3',5,5'-Tetramethylbenzidine (TMB), 3,3'-Diaminobenzidine (DAB), 2,2'-azino-bis(3-ethylbenzothiazoline-6-sulphonic acid) (ABTS), o-phenylenediamine, e.g., o-phenylenediamine dihydrochloride (OPD), 3-amino-9-ethylcarbazole (AEC), homovanillic acid or luminol.

In a), the present kits can comprise peroxidase substrate at any suitable stock concentration. For example, in a), the peroxidase substrate, e.g., ADHP, can have a stock concentration ranging from about 0.01 mg/ml to about 10 mg/ml, e.g., at about 0.01 mg/ml, 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, or 10 mg/ml, or any subrange thereof.

In b), the present kits can comprise hydrogen peroxide at any suitable stock concentration. For example, in b), the hydrogen peroxide can have a stock concentration ranging from about 1% (w/w) to about 50% (w/w), e.g., at about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), or 50% (w/w), or any subrange thereof.

The solution or suspension can have any suitable basic pH. For example, the solution or suspension can have a pH of 12 or higher, e.g., a pH of 12, 13, or 14. The solution or suspension can have any suitable base, e.g., NaOH, KOH or LiOH. The solution or suspension can have any suitable level or concentration of a base. For example, the solution or suspension can have a base, e.g., NaOH, KOH or LiOH, at a level or concentration from about 0.01 mM to about 500 mM, e.g., at about 0.01 mM, 0.1 mM, 1 mM, 10 mM, 20 mM, 30 mM, 40 mM, 50 mM, 60 mM, 70 mM, 80 mM, 90 mM, 100 mM, 200 mM, 300 mM, 400 mM, or 500 mM, or any subrange thereof.

The solution or suspension can have any suitable detergent or surfactant. For example, the solution or suspension can contain a surfactant, e.g., an anionic surfactant, a cationic surfactant, a zwitterionic surfactant or a nonionic surfactant. The solution or suspension can contain any suitable level or concentration of a detergent or surfactant. For example, the solution or suspension can contain a base, e.g., Triton X-100, at a concentration ranging from rom about 0.01% (w/w) to about 10% (w/w), e.g., at about 0.01% (w/w), 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 2% (w/w), 3% (w/w), 4% (w/w), 5% (w/w), 6% (w/w), 7% (w/w), 8% (w/w), 9% (w/w), or 10% (w/w), or any subrange thereof.

In some embodiments, the solution or suspension can contain both a base and a detergent or surfactant. For example, the solution or suspension can contain both NaOH and Triton X-100.

In some embodiments, the present kits can further comprise hemoglobin with known amount and/or concentration configured to prepare a hemoglobin reference standard. The present kits can comprise hemoglobin at any suitable level or concentration. For example, the present kits can comprise hemoglobin at a level or concentration ranging from about 0.5 µg/ml to about 500 µg/ml, e.g., at about 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, or any subrange thereof, of hemoglobin.

The present kits can be configured or used for any suitable purpose. For example, the present kits can be configured or used to monitor hemoglobin amount and/or concentration in a process for reducing or removing hemoglobin. In some embodiments, the process is configured to prepare a cellular membrane preparation from a hemoglobin-containing cell, e.g., a process configured to prepare a red blood cell membrane preparation from the red blood cell. In other embodiments, the process is configured to prepare a cellular membrane coated nanoparticle, said nanoparticle comprising an inner core comprising a non-cellular material and an outer surface comprising a cellular membrane derived from a hemoglobin-containing cell, e.g., a process configured to prepare a red blood cell membrane coated nanoparticle. The cellular membrane coated nanoparticle can be comprised in any suitable composition, e.g., a pharmaceutical composition comprising an effective amount of the cellular membrane coated nanoparticle and a pharmaceutically acceptable carrier and excipient.

In some embodiments, the present kits can further comprise an instruction for using the kit.

In another aspect, the present invention provides a system for quantifying hemoglobin in a sample, which system comprises: a) a kit as described above; and b) means for assessing a peroxidase substrate and/or an oxidation product of said peroxidase substrate, e.g., 7-hydroxyphenoxazin-3-one, to quantify hemoglobin in a sample.

The present systems can comprise any suitable means for assessing the peroxidase substrate and/or the oxidation product, e.g., 7-hydroxyphenoxazin-3-one. For example, the means for assessing the peroxidase substrate and/or the oxidation product, e.g., 7-hydroxyphenoxazin-3-one, can comprise a colorimetric detection instrument. In another example, the means for assessing the peroxidase substrate and/or the oxidation product, e.g., 7-hydroxyphenoxazin-3-one, can comprise a fluorescent detection instrument.

The present kits and systems can be configured or used to quantify hemoglobin in any suitable sample, e.g., a sample as described in the above Section B. The kits and systems can be configured or used to quantify any suitable hemoglobin in a sample, e.g., any suitable type or subtype human hemoglobin, a combination thereof, or a total level thereof, as described in the above Section B. The present kits and systems can be configured or used to quantify a total level of human hemoglobin in a sample. The

D. Example

Experimental Design and Methods

Test and Control Articles

Test and Control Articles include: processed RBC membrane MA50, MA81; black, clear bottom nonbinding 96 well plate with flat bottom such as greiner bio-one 655906; manufactured nanosponge NS61, NS63; micro Plate reader: spectraMax M4, Molecular Devices; OxiRed (Biovision #1572-5); and hydrogen peroxide 30%, VWR Analytical (#BDH7690-1).

Test Methods

A new exemplary fluorogenic hemoglobin assay has been developed. The new exemplary fluorogenic hemoglobin assay has been used to qualify hemoglobin impurity quantification purpose for our TFF process for preparing RBCs membrane as well as a process for preparing the final RBC coated nanosponge products.

Experimental Design

The new exemplary fluorogenic hemoglobin assay has been evaluated to determine its specificity, linearity, limits of detection (LOD), limits of quantitation (LOQ), range, accuracy, and precision in qualifying hemoglobin impurity on RBC coated nanosponge as well as RBC membrane as In-Process Control (IPC).

Procedures

Assay Reagents and Working Solution

Samples preparation solution contains 20 mM NaOH and 0.8% Triton X-100. Hemoglobin standard and test samples are dissolve into this sample solution. OxiRed solution is made by adding 2 ml of DMSO into 5 mg vial of OxiRed. OxiRed solution is protected from light.

Preparation of Hemoglobin Standards

The new exemplary fluorogenic hemoglobin assay is a complete plate-based fluorescent assay in the presence of 20 mM NaOH and 0.8% Triton X-100, which eliminates potential peroxide activity in the assay samples, if any. The assay uses hemoglobin as standards directly instead of hemin and the fluorescent EX/EM at 535 nm/587 nm. The assay has an assay range of 5-100 µg/ml.

Twenty eight and point one mg (28.1 mg) of hemoglobin (Sigma H7379, Lot #SLBQ4742V, 0.32% iron) (hemoglobin is supposed in 0.34655% iron, net weight is 26.0 mg hemoglobin) were weighed and dissolved in 13 ml of a solution containing 20 mM NaOH and 0.8% Triton X-100 to prepare a hemoglobin solution at 2000 µg/ml. A hemoglobin solution at 200 µg/ml is made by a 10-fold dilution in a solution containing 20 mM NaOH and 0.8%:

Make 200 µg/ml×5.0 ml: 4.50 ml of 20 mM NaOH, 0.8% Triton X-100+0.50 ml of 2000 µg/ml hemoglobin.

A series of hemoglobin standard solutions are made as shown in Table 2 below.

TABLE 2

Hemoglobin Standards

| HB Stds | µg/ml | 20 mM NaOH 0.8% Triton X-100 | HB concentration (µg/ml) | Volume ( |
|---|---|---|---|---|
| 1 | 0 | 1000 | 0 | |
| 2 | 5 | 975 | 25 | |
| 3 | 10 | 950 | 50 | |
| 4 | 25 | 875 | 125 | |
| 5 | 50 | 750 | 250 | |
| 6 | 75 | 625 | 375 | |
| 7 | 100 | 500 | 500 | |

Sample Preparation

Red blood cell (RBC) membrane, e.g., human RBC membrane, is generally prepared according to the principles or procedures described in US 2013/337066 A1 or WO 2017/087897 A1. For example, human RBC membrane can be prepared by a process that comprises the steps of lysing red blood cells to obtain a composition comprising RBC membrane and non-membrane cellular moieties, e.g., hemoglobin, and subjecting the composition to tangential flow filtration (TFF) to separate RBC membrane from the non-membrane cellular moieties, e.g., hemoglobin.

RBC membrane coated nanoparticles, e.g., human RBC membrane coated nanoparticles, which contain inner cores comprising a non-cellular material, e.g., poly(lactic-co-glycolic acid) (PLGA), are referred to as nanosponges or NS. The nanosponges are generally prepared according to the principles or procedures described in US 2013/337066 A1 or WO 2017/087897 A1 as well. For example, RBC membrane coated nanoparticles can be prepared by a process that comprises the steps of mixing a nanoparticle inner core comprising a non-cellular material, e.g., PLGA, with cellular membranes derived from red blood cells using a high shear fluid processor to form a nanoparticle comprising the inner core and an outer surface comprising the RBC cellular membrane. The high shear fluid processor can be a microfluidizer (or a microfluidizer processor).

For any assay sample, such as RBC membrane or nanosponge, make a 1:2-1:8 dilution dependent on the concentration, into a solution containing 20 mM NaOH and 0.8% Triton X-100 as follows:

250 µl of RBC membrane or nanosponge
100 µl of 200 mM NaOH
40 µl of 20% Triton X-100
610 µl of H2O The sample can be tested immediately or within 48 hours or even longer.

Assay Procedures

Assay procedures include the following steps:

Add 50 µl of above standards and samples in triplicates into in a black, clear bottom nonbinding 96 wells plate and then cover the plate cover.

Each reaction sample needs 200 µl of reaction mixture. Make the following reaction mixture for 48 samples:

10 ml of 100 mM Phosphate buffer pH 6.5
100 µl of $H_2O_2$ 30%
100 µl of OxiRed at 2.5 mg/ml in DMSO Mix well the reaction mixture and pour into 25 ml reservoir disposable tray. Add 200 µl reaction reagent into each well using multi-channel pipette.

Leave the reaction plate in a plate shaker covered with aluminum foil at 300 rpm at RT and read the fluorescent signal at EX/EM=535/587 nm at exact 15 min.

Calculations and Statistical Methods

All assay standards and samples with different dilutions are tested either in triplicates or in more replicates. With each test result, a standard deviation and percentage standard deviations are calculated. Samples in different dilutions and tested in different dates are compared. All read should be subtracted by the read from plate blank (control) and plot a standard curve with standards of hemoglobin in x axis and corresponding fluorescence reading (FU) as Y axis. Use the Softmax 6.5 software to plot the standard curve. For this particular assay, we found that a 4-parameter curve fit better than linear curve fit most of the time. The concentration of the samples is calculated automatically according to the standard curve. Each sample tested should be in triplicates and calculated percentage deviations should be within 5-8% of range and test should be repeated if it is out of this range. In most of cases, the 5% calculated percentage deviations can be reached easily.

Results and Discussion

Specificity

The specificity of the assay method was investigated by determining whether reaction background in the blank of the assay solution or any of the membrane sample matrix control P1 or nanosponge matrix control P2 should read no more than (NMT) 25% of the lowest standard's reading. Table 3 is a summary showing that the assay reagent 20 mM NaOH/0.8% Triton X-100 and membrane sample matrix control P1 or nanosponge matrix control P2 does not interfere with the analyte hemoglobin quantification.

TABLE 3

Specificity of Fluorogenic Hemoglobin assay

| Specificity | Reading 1 (FU) | Reading 2 (FU) | Reading 3 (FU) | Average | Acceptance criteria (% interference) | % interference | Pass/Fail |
|---|---|---|---|---|---|---|---|
| Value of lowest standards (2.5 µg/ml) | 2293.4 | 2179.4 | 2261.3 | 2244.70 | | | |
| Interference of Standard dilution solution | 432.54 | 421.75 | 369.91 | 408.07 | <25% | 18.18 | Pass |
| Interference of Matrix control P1 | 325.94 | 318.21 | 304.86 | 316.34 | <25% | 14.09 | Pass |
| Interference of Matrix control P2 | 265.7 | 261.94 | 263.07 | 263.57 | <25% | 11.74 | Pass |

Range, Linearity, Relative Standard Deviation and Accuracy

Standard solutions prepared at seven concentrations, typically 5, 10, 15, 25, 50, 75 and 100 µg/ml were assayed for linearity, and the target concentration of the test samples should be around 5-100 µg/m. FIG. 2 shows the linearity range of the assay. Three individually prepared replicates at each concentration were analyzed.

The correlation coefficient for seven concentration levels should be >0.99 for the range of 80 to 120% of the target concentration. A relative standard deviation (CV) is NMT (no more than) 5% for the triplicates results of the suitability standards solutions. The calculated concentration of suitability standard solution must be within 90-110% of the theoretical concentration. As shown in FIG. 3, the correlation coefficient ($R^2$) is 1 and relative standard deviation (CV) is NMT (no more than) 5% for the triplicates results of the suitability standards solutions and calculated accuracy with 95-106%.

Spiked Accuracy

In spiked accuracy test, test samples were tested by adding extra hemoglobin standards in the amount of 75-150% of the target concentration. Three individually prepared replicates at each concentration will be analyzed. The spiked hemoglobin standards should be recovered within 90-110%. Table 4 shows the spiked accuracy of the assay that spiked hemoglobin standards were recovered between 90-100%.

Precision—Repeatability

Sample solutions containing the target level of analyte (10~50 µg/ml) from 1:8800 diluted packed RBCs and 1:4 diluted were prepared. Nine replicates were tested for those samples solution according the procedure. The typical relative standard deviation (CV) of the test subjects show less than 5% percentage standard deviations shown in FIG. 4.

Limit of Detection (LOD) and Limit of Quantitation (LOQ)

Limit of detection (LOD) was determined by sequentially diluting the lowest concentration of standards. Six replicates will be tested from the same series dilutions. FIG. 4 demonstrates the calculated accuracy of series dilutions of 15 µg/ml standards hemoglobin with the LOD around 5.0 µg/ml.

Limit of quantitation (LOQ), the lowest concentration at which an analyte in the sample matrix, can be determined with the accuracy and precision required for the method in question. This value may be the lowest concentration in the standard curve. FIG. 6 shows the results of fluorogenic hemoglobin assay with 1:2 series diluted of TFF RBC membrane MA49 and nanosponge NS63 in six replicates. It shows that the LOQ of this fluorogenic hemoglobin assay is around 10 µg/ml. Table 5 is the summary of the LOQ tests shown LOQ set at 10 µg/ml.

TABLE 4

Spiked Accuracy of the Assay was Evaluated on 1:4 Diluted Nanosponge NS63 Spiked with 75-150% Hemoglobin Standards

| | µg/ml | SD | CV |
|---|---|---|---|
| NS63-4 | 13.841 | 0.549 | 1.7 |

| | Spike | NS63-4 | % Spike | Spiked (µg/ml) HB | Found | Measured | SD | CV | Recovery % |
|---|---|---|---|---|---|---|---|---|---|
| S1 | 5 µl * 100 µg/ml | 45 µl of 1:4 | 75 | 10 | 9.3556 | 21.268 | 0.114 | 0.3 | 93.56 |
| S2 | 42.5 µl * 100 µg/ml | 42.5 µl of 1:4 | 100 | 15 | 14.9044 | 26.155 | 0.47 | 1.1 | 99.36 |
| S3 | 5 µl * 200 µg/ml | 45 µl of 1:4 | 150 | 20 | 19.8156 | 31.728 | 1.009 | 2 | 99.08 |

TABLE 5

Summary of the LOQ Tests Shown LOQ Set at 10 µg/ml

| Samples | Dilutions | µg/ml | SD | CV | AdjConc (µg/ml) | Average (mg/ml) | Stdev | CV (%) |
|---|---|---|---|---|---|---|---|---|
| MA49 | 2 | 29.171 | 0.536 | 1.8 | 58.343 | 67.24 | 0.02 | 0.03 |
| | 4 | 16.807 | 0.373 | 2.2 | 67.23 | | | |
| | 8 | 8.407 | 0.242 | 2.9 | 67.254 | | | |
| | 16 | 1.375 | 0.763 | 16 | 21.997 | | | |
| NS63 | 4 | 13.602 | 0.388 | 2.9 | 54.406 | 53.79 | 0.88 | 1.63 |
| | 8 | 6.646 | 0.44 | 6.6 | 53.167 | | | |
| | 16 | 2.324 | 0.364 | 15.7 | 37.18 | | | |
| | 32 | <LOD | | | | | | |

Assay Reliability

The assay reliability was demonstrated by assaying the exact sample in three different dates and showing similar results in FIG. 7. Table 6 is a summary of reliability of the fluorogenic hemoglobin assay demonstrated that the results of the same test sample assayed in three different date give less than 2% percentage standard deviations (CV).

TABLE 6

Summary of Reliability of the Fluorogenic Hemoglobin Assay

| Test date | Samples | µg/ml | SD | CV | Average (mg/ml) | Stdev | CV (%) |
|---|---|---|---|---|---|---|---|
| Feb. 25, 2017 | NS63-4 | 55.364 | 0.549 | 4.00 | 54.47 | 0.86 | 1.58 |
| Feb. 27, 2017 | NS63-4 | 54.406 | 0.388 | 2.90 | | | |
| Feb. 28, 2017 | NS63-4 | 53.647 | 0.257 | 1.90 | | | |

Protocol Deviations and Impact

Each sample tested should be in triplicates and calculated percentage deviations should be within 5% of range and test should be repeated if it is out of this range. In most of cases, the 2% calculated percentage deviations can be reached easily.

SUMMARY AND CONCLUSIONS

This study shows that the exemplary fluorogenic hemoglobin assay fits well for the quantification of hemoglobin impurity in the TFF processed Red Blood Cell (RBC) membrane and RBC coated nanosponge. The specificity, linearity, limits of detection (LOD) and limits of quantification (LOQ) have been evaluated and the results are as follows:

The specificity of the fluorogenic hemoglobin assay shows that sample solution 20 mM NaOH/0.8% Triton X-100 does not interfere with hemoglobin quantification on TFF RBC membrane as well as nanosponge.

The assay itself uses hemoglobin instead of hemin as assay standards, the targeted assay concentration is set to 10-100 µg/ml and the range of the standards are set to 5-100 µg/ml.

The coefficient of determination ($R^2$) of this fluorogenic hemoglobin assay can be achieved to 0.99 easily with 4-parameter curve fit and back calculated accuracy reach 90%-110%.

The spiked accuracy of this fluorogenic hemoglobin assay on nanosponge reaches 80-120% recovery.

The precision of this fluorogenic hemoglobin assay is less than 10% relative standards deviations on both TFF RBC membrane and nanosponge.

Under current assay procedure, the limit of detection (LOD) is around 5.0 µg/ml and limit of quantification (LOQ) is 10.0 µg/ml.

The exact same test samples tested in three different dates give the results with 5% percentage standard deviations, demonstrating the assay reliability.

This exemplary assay is a complete 96-well plate based fluorescent assay with samples in the condition of 20 mM NaOH and 0.8% Triton X-100, which eliminates the potential peroxide activity in the assay samples, if any. This method has advantages over the commercial Sigma Hemoglobin Assay Kit (Cat #MAK115) on sensitivity, range of the test, LOD, LOQ etc. This improved fluorogenic hemoglobin assay fits well for the hemoglobin quantification in the TFF processed RBC membrane and final product of nanosponge.

REFERENCES

Certain References are listed below.
Nguyen Tien Huy, Dai Thi Xuan Trang, Dinh Thanh Uyen, Motohiro Sasai, Shigeharu Harada, Kaeko Kamei (2005) An improved colorimetric method for quantitation of heme using tetramethylbenzidine as substrate. Anal. Biochem. 344: 289-291.
Shaklai N, Shviro Y, Rabizadeh E, Kirschner-Zilber I. (1985) Accumulation and drainage of hemin in the red cell membrane. Biochim Biophys Acta. 821(2):355-66.
Pandey A V1, Joshi S K, Tekwani B L, Chauhan V S. (1999) A colorimetric assay for heme in biological samples using 96-well plates. Anal Biochem. 268(1):159-61.
Instruction manual: 1-Step™ Ultra TMB-ELISA Substrate Solution, ThermoFisher (Cat #34028)
BioVision sells a Hemin assay kit (Catalog #: K672)

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for quantifying hemoglobin in a sample, which method comprises: a) contacting a sample containing or suspected of containing hemoglobin with a peroxidase substrate and hydrogen peroxide, under suitable conditions, for allowing oxidation of said peroxidase substrate to form an oxidation product; and b) assessing said peroxidase substrate and/or said oxidation product to quantify hemoglobin in said sample, wherein the sample comprises a cellular membrane coated nanoparticle, said nanoparticle comprising an inner core comprising a non-cellular material and an outer surface comprising a cellular membrane derived from a hemoglobin-containing cell.

2. The method of claim 1, wherein the peroxidase substrate is a chromogenic/colorimetric substrate, a fluorogenic substrate or a chemiluminescence substrate.

3. The method of claim 1, wherein the peroxidase substrate is selected from the group consisting of 10-acetyl-3,7-dihydroxyphenoxazine (ADHP), 3,3',5,5'-Tetramethylbenzidine (TMB), 3,3'-Diaminobenzidine (DAB), 2,2'-azino-bis(3-ethylbenzothiazoline-6-sulphonic acid) (ABTS), o-phenylenediamine, e.g., o-phenylenediamine dihydrochloride (OPD), 3-amino-9-ethylcarbazole (AEC), homovanillic acid and luminol.

4. The method of claim 1, wherein the sample is derived from human blood.

5. The method claim 1, wherein the sample comprises a cellular membrane preparation from a hemoglobin-containing cell.

6. The method of claim 5, wherein the hemoglobin-containing cell is a red blood cell.

7. The method of claim 6, wherein the mammalian red blood cell is a human red blood cell.

8. The method of claim 1, wherein the inner core supports the outer surface.

9. The method of claim 1, wherein the cellular membrane comprises a plasma membrane derived from a red blood cell.

10. The method of claim 1, wherein the hemoglobin is a human hemoglobin.

11. The method of claim 1, wherein, the sample is incubated in a solution or suspension that has basic pH and/or contains a detergent before being contacted with a peroxidase substrate, e.g., ADHP, and hydrogen peroxide.

12. The method of claim 11, wherein the solution or suspension contains a surfactant, e.g., an anionic surfactant, a cationic surfactant, a zwitterionic surfactant or a nonionic surfactant.

13. The method of claim 11, wherein the sample is incubated in the solution or suspension for at least about 1 minute before being contacted with a peroxidase substrate, e.g., ADHP, and hydrogen peroxide.

14. The method of claim 1, wherein, in a), the sample has a total protein concentration ranging from 5 µg/m to about 100 mg/ml.

15. The method of claim 1, wherein, in a), the peroxidase substrate, e.g., ADHP, has a final concentration ranging from about 0.1 µg/ml to about 100 µg/ml.

16. The method of claim 1, wherein, in a), the hydrogen peroxide has a final concentration ranging from about 0.001% (w/w) to about 30% (w/w).

17. The method of claim 1, wherein, in a), the sample is contacted with the peroxidase substrate, e.g., ADHP, and hydrogen peroxide in a reaction mixture having a pH ranging from about 5 to about 10.

18. The method of claim 1, wherein the oxidation product, e.g., 7-hydroxyphenoxazin-3-one, is assessed via colorimetric detection and/or fluorescent detection.

19. The method of claim 1, which is used to determine the amount and/or concentration of hemoglobin in a sample.

20. The method of claim 1, which is used to monitor hemoglobin amount and/or concentration in a process for reducing or removing hemoglobin.

21. A kit for quantifying hemoglobin in a sample, which kit comprises: a) a peroxidase substrate; b) hydrogen peroxide; and c) a solution or suspension that has basic pH and/or contains a surfactant for preparing a sample, wherein the sample comprises a cellular membrane coated nanoparticle, said nanoparticle comprising an inner core comprising a non-cellular material and an outer surface comprising a cellular membrane derived from a hemoglobin-containing cell.

22. A system for quantifying hemoglobin in a sample, which system comprises:
   a) a kit of claim 21; and
   b) means for assessing a peroxidase substrate and/or an oxidation product of said peroxidase substrate, e.g., 7-hydroxyphenoxazin-3-one, to quantify hemoglobin in said sample.

* * * * *